Figure 2:
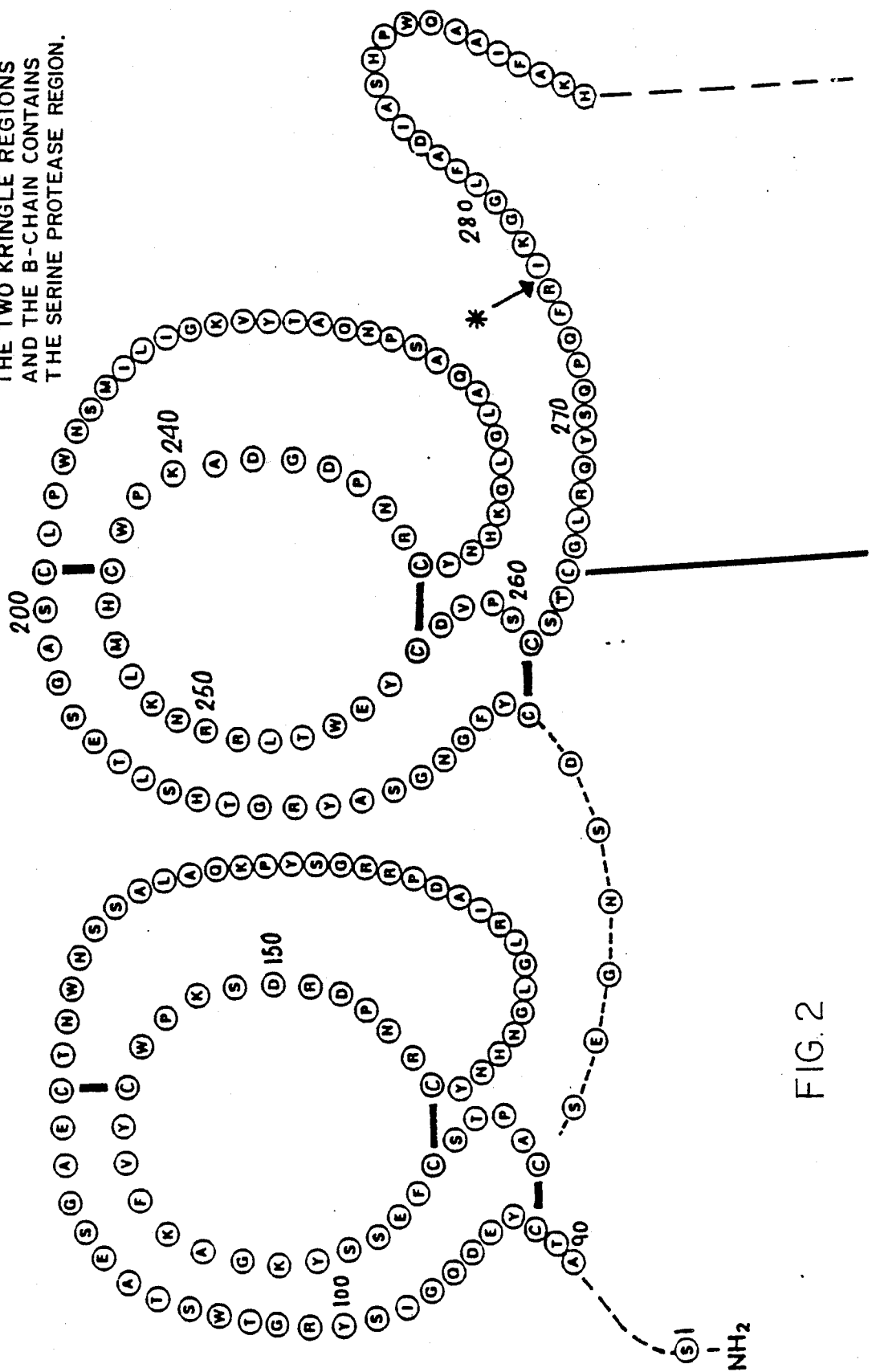
Figure 2A:
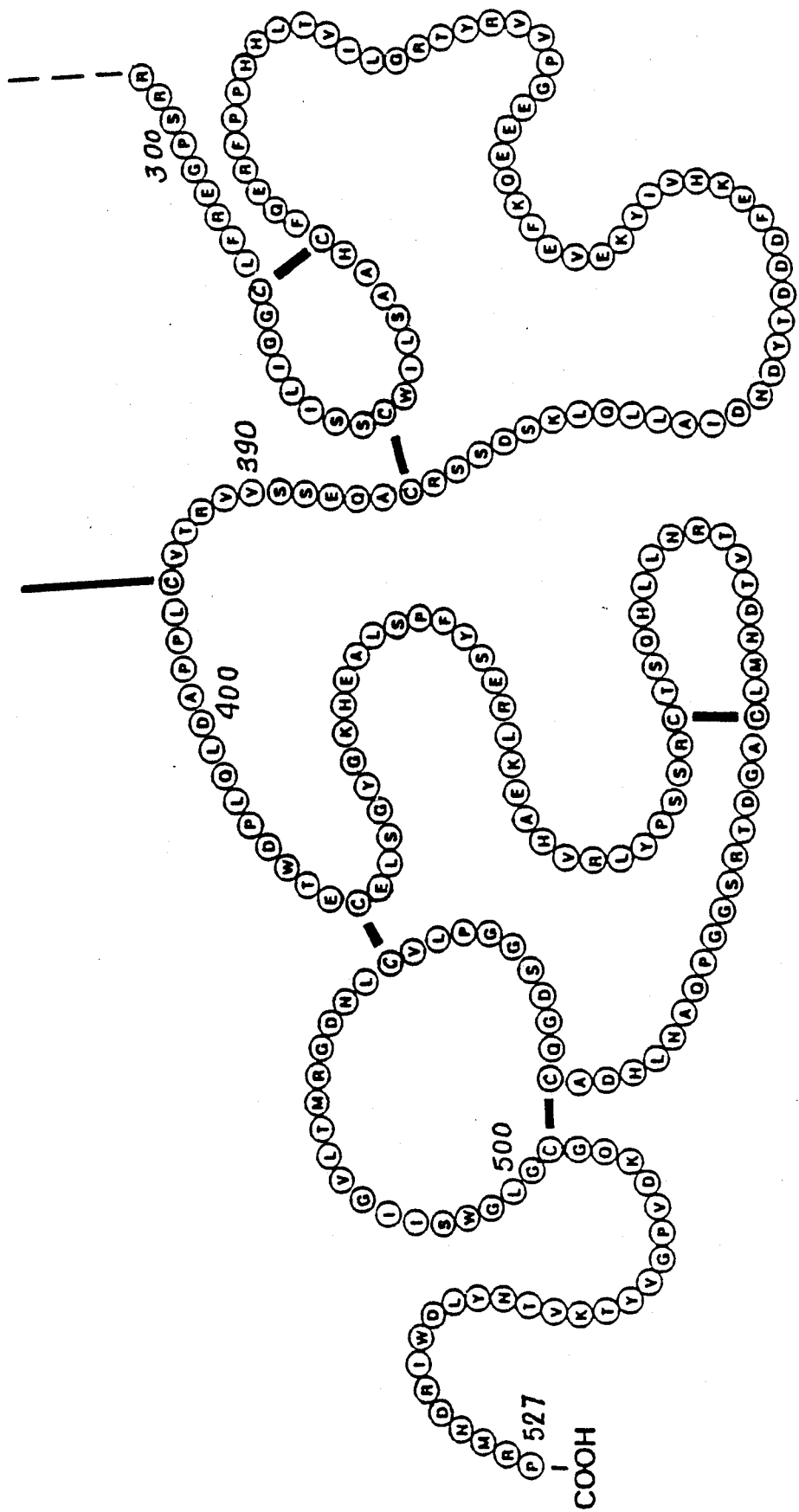
Figure 3:
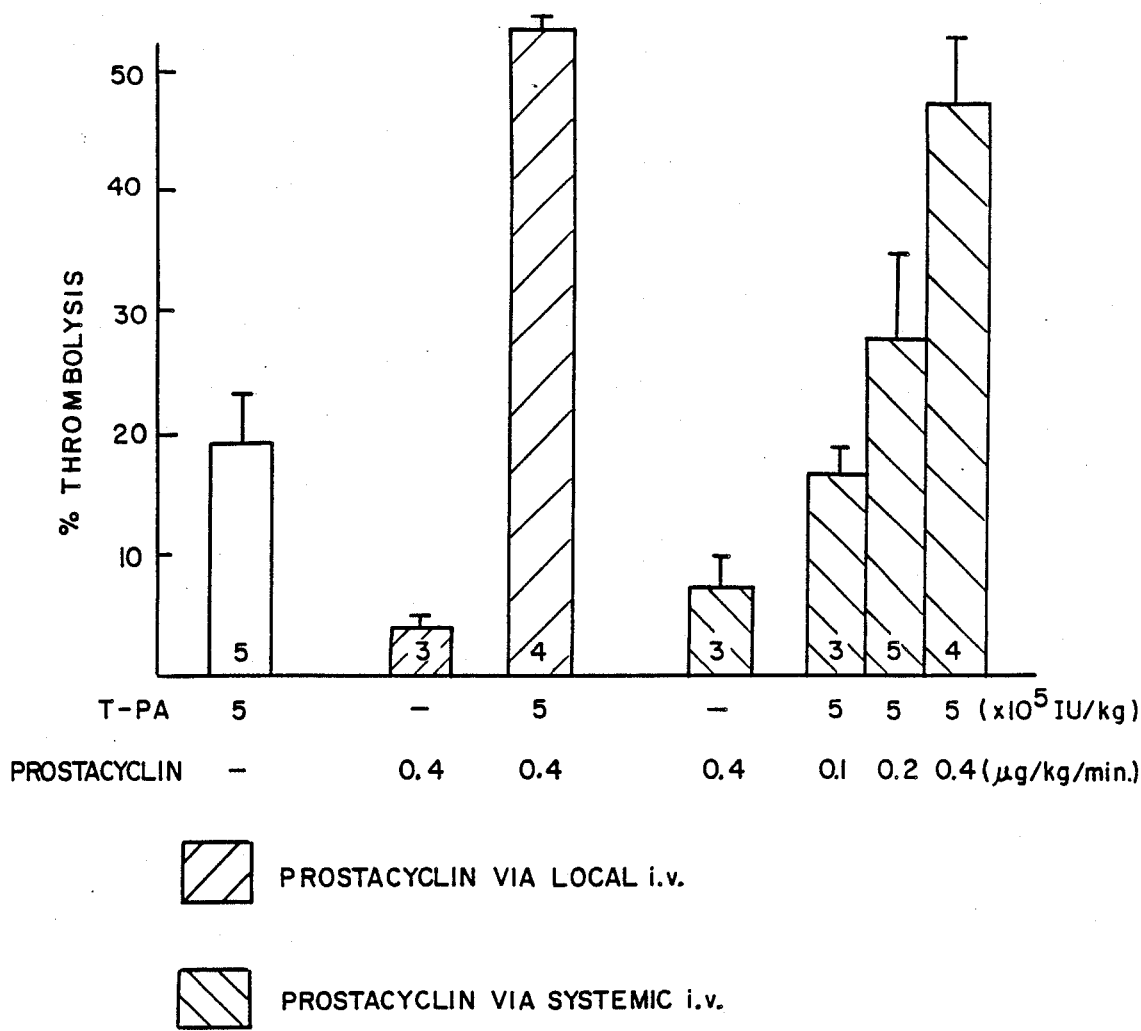

United States Patent [19]

Johnston et al.

[11] Patent Number: 4,929,444
[45] Date of Patent: May 29, 1990

[54] LOW PH PHARMACEUTICAL FORMULATION CONTAINING T-PA

[75] Inventors: Michael D. Johnston, Beckenham, England; Henry Berger, Cary, N.C.

[73] Assignee: Burroughs Wellcome Co., Research Triangle Park, N.C.

[21] Appl. No.: 862,817

[22] Filed: May 13, 1986

[30] Foreign Application Priority Data

May 28, 1985 [GB] United Kingdom ............... 8513358
Aug. 31, 1985 [GB] United Kingdom ............... 8521705

[51] Int. Cl.$^5$ ................................. A61K 37/547
[52] U.S. Cl. ........................ 424/94.64; 424/94.63
[58] Field of Search ................. 424/94.63, 94.64; 530/324; 435/187, 188, 212

[56] References Cited

U.S. PATENT DOCUMENTS

| | | | |
|---|---|---|---|
| 3,998,947 | 12/1976 | D'Hinterland et al. | 424/94.64 |
| 4,505,893 | 3/1985 | Mori et al. | 424/94.64 |
| 4,568,544 | 2/1986 | Hasegawa et al. | 424/94.1 |
| 4,766,075 | 8/1988 | Goeddel et al. | 435/219 |

FOREIGN PATENT DOCUMENTS

0100982 2/1984 European Pat. Off.
0217379 4/1987 European Pat. Off.
2051075 1/1981 United Kingdom.
2138824 5/1984 United Kingdom.

OTHER PUBLICATIONS

Danø et al, Biochimica et Biophysica Acta, 613 (1980) 542–555.
Remington's Pharmaceutical Sciences, Fifteenth Edition (1975), pp. 273–274.
Camiolo et al, cited in Biol. Abstracts 76(2)883 Ref. No. 8252 (1982).
Rote Liste, 1985.
J. Biol. Chem., 254(6) pp. 1998–2003, 1979, Binder, et al.
J. Biol. Chem., 256(13), 7035–7041, 1981.
Hamaguchi, Mie Medical Journal, vol. XXXIII, No. 1, 1983, pp. 57 and 66 to 67, Partial Purification and Properties of Tissue-Type Plaminogen Activator from Nasal and Maxillary Mucosae.
Collen, et al., Biological Properties of Human Tissue-Type Plasminogen Activator Obtained by Expression of Recombinant DNA in Mammalian Cells, The Journal of Pharmacology and Experimental Therapeutics, pp. 146–152, vol. 231, 1984.
Hoylaerts, et al., Kinetics of the Activation of Plasminogen by Human Tissue Plasminogen Activator, pp. 2912–2919, Journal of Biological Chemistry, vol. 257, No. 6, Mar. 25, 1982.

*Primary Examiner*—Jacqueline M. Stone
*Attorney, Agent, or Firm*—Donald Brown

[57] ABSTRACT

A lyophilized pharmaceutical formulation of tissue plasminogen activator and a process for its preparation by vaccum drying a frozen aqueous solution of thereof, in which the pH is from 2 to 5.

22 Claims, 4 Drawing Sheets

```
Ser Tyr Gln Val Ile Cys Arg Asp Glu Lys Thr Gln Met Ile Tyr Gln Gln His Gln Ser
 1
Trp Leu Arg Pro Val Leu Arg Ser Asn Arg Val Glu Tyr Cys Trp Cys Asn Ser Gly

Arg Ala Gln Cys His Ser Val Pro Val Lys Ser Cys Ser Glu Pro Arg Cys Phe Asn
                                       50
Gly Gly Thr Cys Gln Gln Ala Leu Tyr Phe Ser Asp Phe Val Cys Gln Cys Pro Glu

Gly Phe Ala Gly Lys Cys Cys Glu Ile Asp Thr Arg Ala Thr Cys Tyr Glu Asp Gln

Gly Ile Ser Tyr Arg Gly Thr Trp Ser Thr Ala Glu Ser Gly Ala Glu Cys Thr Asn Trp
              100
Asn Ser Ser Ala Leu Ala Gln Lys Pro Tyr Ser Gly Arg Arg Pro Asp Ala Ile Arg

Leu Gly Leu Gly Asn His Asn Tyr Cys Arg Asn Pro Asp Arg Asp Ser Lys Pro Trp
                                                   150
Cys Tyr Val Phe Lys Ala Gly Lys Tyr Ser Ser Glu Phe Cys Ser Thr Pro Ala Cys

Ser Glu Gly Asn Ser Asp Cys Tyr Phe Gly Asn Gly Ser Ala Tyr Arg Gly Thr His

Ser Leu Thr Glu Ser Gly Ala Ser Cys Leu Pro Trp Asn Ser Met Ile Leu Ile Gly Lys
                       200
Val Tyr Thr Ala Gln Asn Pro Ser Ala Gln Ala Leu Gly Leu Gly Lys His Asn Tyr

Cys Arg Asn Pro Asp Gly Asp Ala Lys Pro Trp Cys His Met Leu Lys Asn Arg Arg
                                                               250
Leu Thr Trp Glu Tyr Cys Asp Val Pro Ser Cys Ser Thr Cys Gly Leu Arg Gln Tyr

Ser Gln Pro Gln Phe Arg Ile Lys Gly Gly Leu Phe Ala Asp Ile Ala Ser His Pro Trp

Gln Ala Ala Ile Phe Ala Lys His Arg Arg Ser Pro Gly Glu Arg Phe Leu Cys Gly
                               300
Gly Ile Leu Ile Ser Ser Cys Trp Ile Leu Ser Ala Ala His Cys Phe Gln Glu Arg Phe

Pro Pro His His Leu Thr Val Ile Leu Gly Arg Thr Tyr Arg Val Val Pro Gly Glu Glu

Glu Gln Lys Phe Glu Val Glu Lys Tyr Ile Val His Lys Glu Phe Asp Asp Asp Thr
350
Tyr Asp Asn Asp Ile Ala Leu Leu Gln Leu Lys Ser Asp Ser Ser Arg Cys Ala Gln

Glu Ser Ser Val Val Arg Thr Val Cys Leu Pro Pro Ala Asp Leu Gln Leu Pro Asp
                                               400
Trp Thr Glu Cys Glu Leu Ser Gly Tyr Gly Lys His Glu Ala Leu Ser Pro Phe Tyr

Ser Glu Arg Leu Lys Glu Ala His Val Arg Leu Tyr Pro Ser Ser Arg Cys Thr Ser

Gln His Leu Leu Asn Arg Thr Val Thr Asp Asn Met Leu Cys Ala Gly Asp Thr Arg
                           450
Ser Gly Gly Pro Gln Ala Asn Leu His Asp Ala Cys Gln Gly Asp Ser Gly Gly Pro

Leu Val Cys Leu Asn Asp Gly Arg Met Thr Leu Val Gly Ile Ile Ser Trp Gly Leu
                                                              500
Gly Cys Gly Gln Lys Asp Val Pro Gly Val Tyr Thr Lys Val Thr Asn Tyr Leu Asp

Trp Ile Arg Asp Asn Met Arg Pro
                 527
```

FIG. 1

*SITE OF CLEAVAGE IN ONE-CHAIN t-PA TO GIVE TWO-CHAIN t-PA IN WHICH THE A-CHAIN CONTAINS THE TWO KRINGLE REGIONS AND THE B-CHAIN CONTAINS THE SERINE PROTEASE REGION.

LOW PH PHARMACEUTICAL FORMULATION CONTAINING T-PA

The present invention relates to tissue plasminogen activator and in particular to pharmaceutical formulations containing tissue plasminogen activator, their preparation, and their use in human and veterinary medicine.

It is believed that there is a dynamic equilibrium between the enzyme system capable of forming blood clots—the coagulation system—and the enzyme system capable of dissolving blood clots—the fibrinolytic system—which maintains an intact patent vascular bed. To limit loss of blood from injury, blood clots are formed in the injured vessels. After natural repair of the injury, the superfluous blood clots are dissolved through operation of the fibrinolytic system. Occasionally, blood clots form without traumatic injury and may lodge in major blood vessels resulting in a partial or even total obstruction to blood flow. When this occurs in the heart, lung or brain, the result may be a myocardial infarction, pulmonary embolism or stroke. These conditions combined are the leading cause of morbidity and mortality in the industrialised nations.

Blood clots consist of a fibrous network that is capable of dissolution by the proteolytic enzyme, plasmin. The enzyme is derived from the inactive proenzyme, plasminogen, a component of blood plasma, by the action of a plasminogen activator. There are two immunologically distinct mammalian plasminogen activators. Intrinsic plasminogen activator, also known as urokinase, is an enzyme produced by the kidney and can be isolated from urine. It can also be prepared from a number of tissue culture sources. Extrinsic plasminogen activator, also known as vascular plasminogen activator and as tissue plasminogen activator (t-PA), can be isolated from many tissue homogenates (notably human uterus), the vascular cell wall and from some cell cultures. In addition to these two kinds of plasminogen activator, there is also a bacterial product, streptokinase, prepared from beta-haemolytic streptococci. A major drawback with both urokinase and streptokinase is that they are active throughout the circulation and not just at the site of a blood clot. They can, for example, destroy other blood proteins, such as fibrinogen, prothrombin, factor V and factor VIII so reducing blood clotting ability and increasing the risk of haemorrhage. In contrast, the biological activity of t-PA is dependent on the present of fibrin to which it binds and where it is activated. Maximum activity is thus developed only at the site of a blood clot, i.e. in the presence of the fibrin network to be dissolved, and this greatly avoids the risk of haemorrhage.

The main route of administration of t-PA is by intravascular infusion, thus requiring the formulation of t-PA as a parenteral solution. In the case of a protein it is preferable to present the drug to the physician or veterinarian as a lyophilised pharmaceutical formulation because of its significant transportation and storage advantages over a liquid formulation. It is, however, important that any such lyophilised formulation is readily convertible into the desired parenteral solution without undue inconvenience and difficulty and that the physician or veterinarian is able to obtain the required concentration of drug in any given situation simply by reconstitution of the formulation in the appropriate amount of solvent. It is, for example, inadvisable to administer a large volume of solution to a patient with a cardiac or renal disorder since it would put the heart or kidneys under even greater stress. The volume should therefore be kept to a minimum in such circumstances. It is thus desirable that a parenteral solution can be obtained not only with a relatively low concentration but also with a high concentration of the drug.

A number of lyophilised pharmaceutical formulations of t-PA have been described in the prior art, for example in EP-A-113 319, and EP-A-123 304. The formulations are prepared from aqueous saline solutions of t-PA, in which the pH is about neutral, and suffer from the disadvantage that the solubility of t-PA in such solutions is low in the absence of an increase in the ionic concentration. Consequently, the parenteral solutions obtained from such lyophilised formulations either contain low concentrations of t-PA, necessitating in some situations the adminsitration of undesiably large volumes of solution to a patient, or they are hypertonic, which on administration may be detrimental to red blood cells.

It has now been found that the solubility of t-PA in an aqueous solution can be improved if the pH of the solution is within an acidic range, that a lyophilised pharmaceutical formulation can be prepared from an acidic solution of t-PA, and that the formulation is capable of affording a parenteral solution which, on administration, presents no significant physiological problems. Accordingly, the present invention provides a process for preparing a lyophilised pharmaceutical formulation of t-PA, which comprises vacuum drying a frozen aqueous solution of t-PA, in which the pH is from 2 to 5.

As a result of the improved solubility of t-PA, a lyophilised pharmaceutical formulation can be prepared in accordance with the present invention that is capable of affording a parenteral solution containing a high concentration of t-PA without any substantial risk of the t-PA being precipitated out of solution. The lyophilised formulation may, therefore, be presented to physicians or veterinarians who can dissolve the formulation, as and when required, to the desired concentration using, for example, water of neutral or acidic pH. The present invention, therefore, provides a stable lyophilised pharmaceutical formulation that allows for greater flexibility in its handling and use by physicians and veterinarians, as well as providing for a more convenient means of transportation and storage.

The t-PA of use with the present invention may be any bioactive protein substantially corresponding to mammalian, and especially human, t-PA and includes forms with and without glycosylation. It may be one- or two-chain t-PA, or a mixture thereof, as described in EP-A-112 122 and, in the case of fully glycosylated human t-PA, has an apparent molecular weight on polyacrylamide gels of about 70,000 and an isoelectric point of between 7.5 and 8.0. Preferably the t-PA has a specific activity of about 500,000 IU/mg (International Units/ml, the International Unit being a unit of activity as defined by WHO, National Institute for Biological Standards and Control, Holly Hill, Hampstead, London, NW3 6RB, U.K.).

The amino acid sequence of t-PA preferably substantially corresponds to that set forth in FIG. 1. The sequence is thus identical to that in FIG. 1 or contains one or more amino acid deletions, substitutions, insertions, inversions or additions of allelic origin or otherwise, the resulting sequence having at least 80% and preferably 90%, homology with the sequence in FIG. 1 and retaining essentially the same biological and immunological properties of the protein. In particular, the t-PA sequence is identical to that in FIG. 1 or has the same sequence but with the amino acid in the 245th position from the serine N-terminus being valine instead of methionine, either sequence optionally being without any of the first three amino acids or optionally having an additional polypeptide N-terminal presequence of Gly-Ala-Arg.

The amino acid sequence set forth in FIG. 1 has thirty-five cysteine residues and thus the potential for forming seventeen disulphide bridges. Based on analogy with other proteins whose structure has been determined in more detail, the postulated structure for the sequence (arising from disulphide bond formation) between the amino acid in the 90th position and the proline C-terminus is set forth in FIG. 2. The structure of the N-terminal region is less certain although some proposals have been put forward (*Progress in Fibrinolysis*, 1983, 6, 269–273; and *Proc. Natl. Acad. Sci.*, 1984, 81, 5355–5359). The most important features of the structure of t-PA are the two kringle regions (between the 92nd and the 173rd amino acids and between the 180th and 261st amino acids), which are responsible for the binding of the protein to fibrin, and the serine protease region, which comprises the major part of the B-chain and which is responsible for the activation of plasminogen. The amino acids of special significance in serine proteases are the catalytic triad, His/Asp/Ser. In t-PA these occur at the 322nd, the 371st and the 463rd positions. The disulphide bridge between the 264th and 395th cysteine amino acid residues is also important in that it holds together the A- and the B-chains in the two-chain form of t-PA.

In FIGS. 1 and 2, the conventional one and three letter codes have been employed for the amino acid residues as follows:

| Asp | D | Aspartic acid | Ile | I | Isoleucine |
|-----|---|---------------|-----|---|------------|
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Trytohan |
| Val | V | Valine | Gln | Q | Glutamine |
| Met | M | Methionine | Asn | N | Asparagine |

The t-PA may be obtained by any of the procedures described or known in the art. For example, it may be obtained from a normal or neoplastic cell line of the kind described in *Biochimica et Biophysica Acta*, 1979, 580, 140–153; EP-A-41 766 or EP-A-113 319. It is preferred, however, that t-PA is obtained from a cultured transformed or transfected cell line, derived using recombinant DNA technology as described in, for example, EP-A-93 619; EP-A-117 059 or EP-A-117 060. It is particularly preferred that Chinese hamster ovary (CHO) cells are used for the production of t-PA and are derived in the manner as described in *Molecular and Cellular Biology*, 1985, 5(7), 1750–1759. In this way, the cloned gene is cotransfected with the gene encoding dihydrofolate reductase (dhfr) into dhfr⁻CHO cells. Transformants expressing dhfr are selected on media lacking nucleosides and are exposed to increasing concentrations of methotrexate. The dhfr and t-PA genes are thus coamplified leading to a stable cell line capable of expressing high levels of t-PA.

The t-PA is, preferably, purified using any of the procedures described or known in the art, such as the procedures described in *Biochimica et Biophysica Acta*, 1979, 580, 140–153; *J. Biol. Chem.*, 1979, 254(6), 1998–2003; ibid, 1981, 256(13), 7035–7041; *Eur. J. Biochem.*, 1983, 132, 681–686; EP-A-41 766; EP-A-113 319 or GB-A-2 122 219.

There does not appear to be any upper limit on the solubility of t-PA in the aqueous solution of use in the process of the present invention. At very high concentrations, such as greater than 150,000,000 IU/ml (International Units/ml), the solution merely becomes viscous without any significant precipitation of the t-PA. The concentration of t-PA in the aqueous solution may vary therefore within wide limits, for example from 50,000 to 50,000,000 IU/ml. In order to secure the maximum advantage from the present invention, it is preferred that the concentration of t-PA is greater than 100,000 IU/ml, more especially greater than 500,000 IU/ml, and most especially greater than 1,000,000 IU/ml. It is most particularly preferred that the concentration of t-PA is about 5,000,000 IU/ml.

The upper limit of the pH of the aqueous solution is, preferably, 4.5. In fact, the pH is, preferably, within the range from 2.5 to 4.0, more preferably from 2.8 to 3.5, and most preferably about 3.0. The desired pH of the aqueous solution is conveniently obtained using a physiologically acceptable inorganic or organic acid. Examples of such an acid include hydrochloric acid, sulphuric acid and nitric acid, and citric acid, tartaric acid and benzenesulphonic acid. Of these examples, hydrochloric acid is preferred.

Although some physiologically acceptable co-solvent may optionally be present in addition to water, it is preferred that the medium for the aqueous solution is wholly or substantially aqueous.

The parenteral solution obtained from the lyophilised pharmaceutical formulation may be hypertonic, hypotonic or isotonic with the blood serum of the patient. To avoid undesirable side effects, however, the parenteral solution is, preferably, isotonic although minor deviations are not of great physiological concern. A substantially isotonic parenteral solution may be obtained by the inclusion of a physiologically acceptable agent that is capable of raising the tonicity of the solution to the required level. The agent may be included within the aqueous solution to be freeze-dried so that it is already present in the lyophilised pharmaceutical formulation or it may be included within the water of neutral or acidic pH that is used to dissolve the formulation to obtain the desired parenteral solution. Examples of such an agent are well known in the art and include dextrose (in anhydrous or monohydrate form) and sodium chloride and mixtures thereof. The concentration of the agent in the aqueous solution or in the water for dissolution will, of course, vary from agent to agent. In the case of sodium chloride, the concentration is perferably from 7 to 10 mg/ml, and most preferably about 8.5 mg/ml, the concentration often referred to as physiological saline solution or just physiological saline. In the case of anhydrous dextrose, the concentration is preferably from 30 to 70 mg/ml, and most preferably about 50 mg/ml.

The aqueous solution may optionally contain additives normally associated with lyophilised pharmaceutical formulations of this type. Examples include human serum albumin, and binders and fillers, such as mannitol, lactose and glucose. In addition, t-PA has a tendency to adsorb to glass and plastic surfaces and, therefore, it may be desirable to include a surface active agent in the aqueous solution to prevent or minimise such adsorption. Examples of such an agent include polyoxyethylene derivatives of fatty acid partial esters of sorbitol anhydrides, such as that marketed under the trade name "Tween 80".

One of the surprising advantages of the present invention, apart from the substantially increased solubility of t-PA, is that the use of an acidic parenteral solution obtained by reconstitution of the lyophilised pharmaceutical formulation does not appear to present any signficant adverse physiological effects on administration to the patient. It would seem that the bloodstream is generally able to raise the pH of the solution to neutral almost as soon as contact is made, the t-PA being rapidly distributed within the bloodstream. It is, however, preferred that this process is not substantially impeded in any way and that the parenteral solution and hence the aqueous solution to be freeze dried and the water for reconstitution do not contain a strong buffering agent. A weak buffering agent, though, that does not significantly inhibit this process may be included and, indeed, at acidic pH t-PA itself acts as its own weak buffering agent. In addition, human serum albumin is capable of acting as weak buffering agent.

Because of the substantially increased solubility of t-PA in an aqueous solution, in which the pH is from 2 to 5, there is no need to include in the parenteral solution, obtained from reconstitution of the lyophilised formulation, any additional material, such as lysine or ornithine or a salt thereof, for enhancing the solubility of t-PA.

The aqueous solution of t-PA may be prepared by obtaining a solution of purified t-PA and exchanging the medium for an aqueous medium having a pH from 2 to 5, or by dissolving purified t-PA in an aqueous medium having a pH from 2 to 5.

The purification of t-PA may involve as a final stage the elution of the protein from a chromatographic column as a solution containing a strong buffering agent. As mentioned previously, it is preferred that the parenteral solution, and hence the lyophilised pharmaceutical formulation and aqueous solution, does not contain a strong buffering agent and, therefore, a convenient means for effecting its removal whilst exchanging the medium is to use dialysis. This may be carried out using dialysis tubing or an artifical kidney in which the purified solution is dialysed against an aqueous medium in which the pH is from 2 to 5. It may be desirable, especially if the concentration of t-PA in the purified solution is high, first to adjust the pH of the solution so that it is from 2 to 5. Another means for effecting the removal of a strong buffering agent whilst exchanging the medium is to subject the purified solution to gel filtration and to develop the column with an aqueous medium in which the pH is from 2 to 5.

t-PA in the form of a precipitated solid may, preferably, be obtained from a purified solution by adjusting the pH to about 5.5, cooling the solution to just above its freezing point, and recovering the protein by, for example, centrifugation. The precipitated solid may then be dissolved in an aqueous medium having a pH from 2 to 5 in a conventional manner.

It is preferred that the resulting aqueous solution is sterilized conventionally, for example, by filter sterilization, and that it is then dispensed into sterile, plastic or glass containers, such as ampoules or vials, in volumes of, for example, from 0.5 to 20 ml.

The aqueous solution of t-PA is frozen, preferably, at a temperature of from −10° to −40° C. The frozen aqueous solution is then, preferably, maintained at this temperaure until the vacuum drying is commenced.

Vacuum drying of the frozen aqueous solution may be carried out conventionally and includes drying under a partial or complete vacuum, for example at from 0.01 to 0.1 Torr, for sufficient time to effect removal of substantially all the frozen liquid.

The temperature at which vacuum drying is carried out is usually from −30° to −40° C. at the beginning of the process so as to maintain the aqueous solution in a substantially or completely frozen form. As the process proceeds and the water is removed, the temperature may be gradually increased until it reaches room temperature. It is preferred, at the end of the process, to carry out the vacuum drying at room temperature or just above under a substantial vacuum of about 0.01 Torr in order to remove as much as possible of the last traces of water. The moisture content of the resulting lyophilised pharmaceutical formulation is preferably less than 2.5%. Once the vacuum drying has been completed, the sterile, plastic or glass container, containing the lyophilised pharmaceutical formulation is then conveniently sealed.

During the vacuum drying of the frozen aqueous solution, the water is removed leaving the t-PA in the form of a physiologically acceptable salt. Accordingly, the present invention also provides a physiologically acceptable salt, especially a physiologically acceptable acid addition salt, such as the hydrochloride salt, of t-PA.

The use of the present invention enables for the first time a lyophilised pharmaceutical formulation to be obtained which is capable of affording a parenteral solution containing a high concentration of t-PA. Accordingly, the present invention also provides a lyophilised pharmaceutical formulation of t-PA, which, on dissolution in water, is capable of affording a concentration of t-PA greater than 100,000 IU/ml, more especially greater than 500,000 IU/ml, and most especially greater than 1,000,000 IU/ml.

To prepare a parenteral solution of t-PA for administration, the lyophilised pharmaceutical formulation obtained according to the process of the present invention is reconstituted in water of neutral or acidic pH. If the aqueous solution from which the lyophilised pharmaceutical formulation was obtained is substantially isotonic, then it is preferred that the water for reconstitution is also substantially isotonic.

The biological activity of t-PA in dissolving the fibrin network of blood clots has led to its utility in the treatment of thrombotic disorders (*The Lancet,* Nov. 7th 1981, 1018–1020; ibid., Apr. 13th 1985, 842–847; *The New England Journal of Medicine,* 1984, 310(10), 609–613; and ibid., 1985, 312(14), 932–936). The present invention, therefore, provides a method for the treatment of a thrombotic disorder in a mammal, which comprises the administration to the mammal of a parenteral solution of t-PA obtained from a lyophilised pharmaceutical formulation, as defined herein. In the alternative, there is also provided a lyophilised pharmaceutical formulation of t-PA, as defined herein, for use in human or veterinary medicine, especially for use in the treatment of a thrombotic disorder.

Particular examples of a thrombotic disorder are known in the art but include myocardial infarction, deep vein thrombosis, pulmonary embolism and stroke.

The main route of administration of t-PA is by intravascular, especially intravenous, infusion although conceivably other routes of administration, such as intramuscular administration, may be enjoyed. Intravascular infusions are normally carried out with the parenteral solution contained within an infusion bag or bottle or within an electrically operated infusion syringe. The solution may be delivered from the infusion bag or bottle to the patient by gravity feed or by the use of an infusion pump. The use of gravity feed infusion systems does not afford sufficient control over the rate of administration of the parenteral solution and, therefore, the use of an infusion pump is preferred especially with solutions containing relatively high concentrations of t-PA. More preferred, however, is the use of an electrically operated infusion syringe which offers even greater control over the rate of administration.

An effective amount of t-PA to treat a mammal with a thrombotic disorder will of course depend upon a number of factors including, for example, the age and weight of the mammal, the precise condition requiring treatment and its severity, the route of administration, and will ultimately be at the discretion of the attendant physician or veterinarian. It is likely, however, that an effective amount for lysing a coronary artery thrombus, for example, will generally be in the range from 150,000 to 450,000 IU/kg bodyweight of patient per hour. Thus, for a 70 kg adult human being, an effective amount per hour will generally be from 10,000,000 to 30,000,000 IU, especially about 20,000,000 IU, and this amount may be administered with or without a priming dose. It is also likely that the dosage will be less for some thrombotic conditions, such as deep vein thrombosis and acute stroke, or for simply maintaining patency of an already reperfused coronary artery. In these situations, an effective amount will generally be from 7,000 to 36,000 IU/kg bodyweight of patient per hour.

The following examples are provided in illustration of the present invention and should not be construed in any way as constituting a limitation thereof.

EXAMPLE 1

A clarified harvest of t-PA, obtained from a cultured transformed CHO cell line which as derived using the procedure of *Molecular and Cellular Biology*, 1985, 5(7), 1750–1759, was purified chromatographically and the t-PA collected as an aqueous solution containing 0.17M sodium citrate and 0.01% (w/v) Tween 80 at a pH of 5.5. The pH of the solution was adjusted to 3.0 with hydrochloric acid and the resulting solution concentrated by ultrafiltration using an H-10 Cartridge (Amicon Ltd., Upper Hill, Stonehouse, Gloucestershire, England). The concentrated aqueous solution was further purified by applying it to a gel filtration column (Sephadex G-150; Pharmacia Biotechnology, Uppsala, Sweden) and eluting with 0.85% saline solution containing 0.01% (w/v) Tween 80 at a pH of 3.0. A highly purified aqueous solution of t-PA was thus obtained which was concenrated once more using a disposable artifical kidney. The t-PA was precipitated out of solution by increasing the pH to 5.5 with sodium hydroxide and maintaining the suspension at 4° C. for 2 hours. The t-PA was recovered by centrifugation at 4000×g for 30 minutes at 4° C. The pellet of t-PA was redissolved in an aqueous solution of sodium chloride (0.85% (w/v)) containing 0.01% (w/v) Tween 80 and adjusted to pH 3.0 with hydrochloric acid. The volume of saline solution used was that required to give a concentration of t-PA between 7,500,000 IU/ml and 10,000,000 IU/ml. This solution of t-PA was diluted with further aqueous solution of sodium chloride (0.85% (w/v)) containing 0.01% (w/v) Tween 80 and adjusted to pH 3.0 with hydrochloric acid, and also with sufficient fo a solution of 10% (w/v) mannitol in the same acid saline solution to give final concentrations of 5,000,000 IU/ml of t-PA and 25 mg/ml of mannitol. The resulting solution was filter sterilized and dispensed in volumes of 1 ml into glass vials which were frozen at −35° C. A vacuum was applied at 0.05 Torr. After about 24 hours, the temperature was gradually increased to 5° C. and maintained at this temperature for 16 hours. It was then increased again to 25° C. and the vacuum increased to 0.02 Torr for a further 24 hours, after which the vials were sealed under a partial vacuum of 600 Torr of dry nitrogen.

EXAMPLE 2

The thrombolytic efficacy of a parenteral solution obtained from the lyophilised formulation of t-PA of Example 1 was evaluated in an in vivo model of jugular vein thrombosis.

(a) Procedure-

The experimental procedure essentially followed that first described by Collen et al (*J. Clin. Invest.*, 1983, 71, 368–376).

The lyophilised formulation of Example 1 rapidly and completely dissolved in sterile isotonic saline adjusted to pH3.0 containing 0.01% Tween 80. A parenteral solution was thus provided for a 2 hour infusion of 500,000 IU/kg of t-PA. Infusion was via a cannula in the right femoral vein. Four New Zealand white rabbits were used in the study. After infusion the degree of thrombolysis was estimated.

(b) Results:

The percentage thrombolysis was 28.9±4.1 thus demonstrating the thrombolytic effect of the parenteral solution obtained from the lyophilised formulation of Example 1. In addition, there were no adverse reactions observed with this solution.

I claim:

1. A lyophilized pharmaceutical formulation of t-PA having been prepared by vacuum drying a frozen sterilized unbuffered aqueous solution of t-PA, in which the pH is from 2 to 5.

2. A formulation according to claim 1, wherein the t-PA has the amino cid sequence set forth in FIG. 1 or has the same amino acid sequence but with the amino acid in the 245th position from the serine N-terminus being valine instead of methionine.

3. A formulation according to claim 1, wherein the t-PA is obtained from a cultured transformed or transfected cell line derived using recombinant DNA technology.

4. A lyophilized pharmaceutical formulation of t-PA having been prepared by vacuum drying a frozen sterilized unbuffered aqueous solution of t-PA, in which the pH is from 2 to 5 and the concentration of t-PA in the aqueous solution is greater than 100,000 IU/ml.

5. A formulation according to claim 4, wherein the concentration of t-PA is greater than 500,000 IU/ml.

6. A formulation according to claim 5, wherein the concentration of t-PA is greater than 1,000,000 IU/ml.

7. A formulation according to claim 6, wherein the concentration of t-PA is about 5,000,000 IU/ml.

8. A formulation according to claim 1, wherein the pH of the aqueous solution is from 2 to 4.5.

9. A formulation according to claim 8, wherein the pH is from 2.5 to 4.0.

10. A formulation according to claim 9, wherein the pH is from 2.8 to 3.5.

11. A formulation according to claim 10, wherein the pH is about 3.0.

12. A formulation according to claim 1, wherein the aqueous solution contains a physiologically acceptable agent that renders the solution substantially isotonic with human blood serum.

13. A formulation according to claim 12, wherein the physiologically acceptable agent is saline.

14. A formulation according to claim 12, wherein the physiologically acceptable agent is dextrose.

15. A formulation according to claim 1, wherein the aqueous solution contains a surface active agent.

16. A lyophilised pharmaceutical formulation of t-PA having been prepared by vacuum drying a frozen sterilized unbuffered aqueous saline solution of t-PA, in which the pH is from 2 to 5.

17. A sealed container of a lyophilised pharmaceutical formulation according to claim 1.

18. A sealed container of a lyophilised pharmaceutical formulation according to claim 16.

19. A method for the treatment of a thrombotic disorder in a mammal, which comprises the administration to the mammal of a parenteral solution of t-PA obtained by reconstitution of a lyophilised pharmaceutical formulation according to claim 1.

20. A method for the treatment of a thrombotic disorder in a mammal, which comprises the administration to the mammal of a parenteral solution of t-PA obtained by reconstitution of a lyophilised pharmaceutical formulation according to claim 16.

21. An acidic lyophilised unbuffered pharmaceutical formulation of t-PA which, when dissolved in water, affords a concentration of t-PA greater than 100,000 IU/ml.

22. A lyophilised pharmaceutical formulation according to claim 21, wherein the concentration is greater than 500,000 IU/ml.

* * * * *